United States Patent [19]

Kinoshita et al.

[11] Patent Number: 5,374,634
[45] Date of Patent: Dec. 20, 1994

[54] PYRIDINE DERIVATIVES

[75] Inventors: Iwao Kinoshita; Yasuo Onoda; Haruki Takai; Nobuo Kosaka; Akio Ishii; Joji Nakamura; Hiroyuki Ishida, all of Shizuoka; Katsushige Gomi, Susono, all of Japan

[73] Assignee: Kyowa Hakko Kogyo Co., Ltd., Tokyo, Japan

[21] Appl. No.: 84,480

[22] Filed: Jul. 1, 1993

[30] Foreign Application Priority Data

Jul. 7, 1992 [JP] Japan .................... 4-180116

[51] Int. Cl.$^5$ ............... A61K 31/495; A61K 31/445; C07D 401/00; C07D 211/78
[52] U.S. Cl. ................. 514/252; 514/227.8; 514/237.2; 514/256; 514/318; 514/354; 544/60; 544/124; 544/130; 544/295; 544/333; 544/360; 546/194; 546/323
[58] Field of Search ............. 544/295, 360, 60, 124, 544/130, 333; 546/323, 194; 514/252, 354, 227.8, 237.2, 256, 318

[56] References Cited

U.S. PATENT DOCUMENTS

| | | | |
|---|---|---|---|
| 3,397,273 | 8/1968 | Van Heyningen et al. | 424/263 |
| 5,112,867 | 3/1992 | Kinoshita et al. | 514/617 |

FOREIGN PATENT DOCUMENTS

| | | |
|---|---|---|
| 0460690 | 12/1991 | European Pat. Off. |
| 130216 | 6/1991 | Japan |
| 9169 | 1/1993 | Japan |

Primary Examiner—Cecilia Tsang
Attorney, Agent, or Firm—Fitzpatrick, Cella, Harper & Scinto

[57] ABSTRACT

There is provided a pyridine derivative represented by the formula (I)

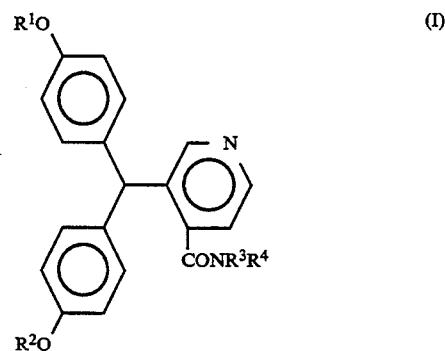

wherein each of $R^1$ and $R^2$ independently represents hydrogen or lower alkyl and each of $R^3$ and $R^4$ independently represents hydrogen, lower alkyl, alicyclic alkyl, substituted or unsubstituted polycyclic alkyl, substituted or unsubstituted aryl, or substituted or unsubstituted heterocyclic group, or $R^3$ and $R^4$ are combined with nitrogen atom adjacent thereto to form a substituted or unsubstituted alicyclic heterocyclic group, or pharmaceutically acceptable salt thereof. The pyridine derivative exhibits bone resorption inhibiting effect and is useful as a medicament for treating osteoporosis.

7 Claims, No Drawings

PYRIDINE DERIVATIVES

BACKGROUND OF THE INVENTION

The present invention relates to pyridine derivatives which are useful as a medicament for treating osteoporosis.

It is disclosed in U.S. Pat. No. 5,112,867 that triphenylmethane derivatives with substituents such as carbamoyl are useful in treating osteoporosis.

SUMMARY OF THE INVENTION

The present invention provides pyridine derivatives represented by the formula (I) (hereinafter referred to as Compound (I); the same designation shall be applied to compounds represented by other formulae):

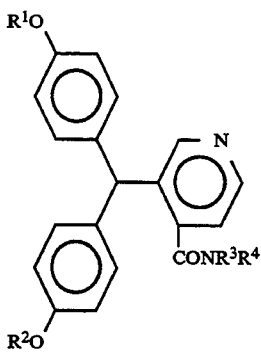

wherein each of $R^1$ and $R^2$ independently represents hydrogen or lower alkyl; and each of $R^3$ and $R^4$ independently represents hydrogen, lower alkyl, alicyclic alkyl, substituted or unsubstituted polycyclic alkyl, substituted or unsubstituted aryl, or substituted or unsubstituted heterocyclic group, or $R^3$ and $R^4$ are combined with nitrogen atom adjacent thereto to form a substituted or unsubstituted alicyclic heterocyclic group, or a pharmaceutically acceptable salt thereof.

DETAILED DESCRIPTION OF THE INVENTION

In the definition of the respective groups in the formula (I), the lower alkyl means a straight or branched alkyl having 1 to 8 carbon atoms, for example, methyl, ethyl, propyl, isopropyl, butyl, isobutyl, sec-butyl, tert-butyl, pentyl, neopentyl, hexyl, heptyl, octyl, etc. The alicyclic alkyl means cycloalkyl having 3 to 8 carbon atoms, for example, cyclopropyl, cyclopentyl, cyclohexyl, cycloheptyl, cyclooctyl, etc. The substituted or unsubstituted polycyclic alkyl includes, for example, tricyclo[3.3.1.1$^{3,7}$]decyl and tricyclo[3.3.1.0$^{3,7}$]nonyl having the structural formula:

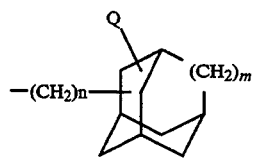

wherein Q represents hydrogen or lower alkyl; m is an integer 0 or 1; and n is integer of 0 to 5; and a bridged saturated hydrocarbon group including bicyclo[2.2.1-]heptyl having the structural formula:

wherein Q and n have the same significance as defined above; the lower alkyl for the definition of Q has the same significance as defined for the lower alkyl mentioned above.

The aryl represents, for example, phenyl, naphthyl, etc. which is optionally substituted with 1 to 3 substituents independently selected from the group consisting of lower alkyl, hydroxy, lower alkoxy, lower alkylthio, halogen, nitro, amino, lower alkanoyl, aroyl, carboxyl, lower alkoxycarbonyl, trifluoromethyl, etc. The lower alkanoyl means straight or branched alkanoyl having 1 to 5 carbon atoms, and includes, for example, formyl, acetyl, propionyl, butyryl, isobutyryl, valeryl, pivaloyl, etc. The lower alkyl and the alkyl moiety in the lower alkoxy, lower alkylthio and lower alkoxycarbonyl have the same meanings as defined above. The aryl moiety in the aroyl has the same significance as defined for aryl. The halogen means fluorine, chlorine, bromine or iodine.

The heterocyclic group includes, for example, an aromatic heterocyclic group such as pyridyl, quinolyl and thiazolyl; or an alicyclic heterocyclic group such as pyrrolidinyl, piperidyl, piperidino, piperazinyl, morpholino and thiomorpholino. The alicyclic heterocyclic group which is formed where $R^3$ and $R^4$ are combined with the nitrogen atom adjacent thereto has the same significance for the alicyclic heterocyclic group as previously defined. The number of the substituents for the heterocyclic group is 1 or 2. The substituents are the same or different, and include, for example, lower alkyl, lower alkoxy, halogen, benzyl, substituted or unsubstituted phenyl, pyridyl, pyrimidyl, etc. The lower alkyl, lower alkoxy and halogen have the same significance as previously defined for the substituent of the aryl as mentioned above. The substituted phenyl means phenyl optionally substituted with 1 to 3 substituents independently selected from the substituents for the substituted aryl as mentioned above.

Pharmaceutically acceptable salts of Compound (I) include acid addition salts such as hydrochloride, hydrobromide, hydroiodide, nitrate, phosphate, formate, acetate, benzoate, maleate, fumarate, succinate, tartrate, citrate, oxalate, glyoxylate, aspartate, methansulfonate, ethanesulfonate, benzenesulfonate, etc.

The process for the preparation of Compound (I) is described below.

Compound (I) is prepared by the following reaction steps:

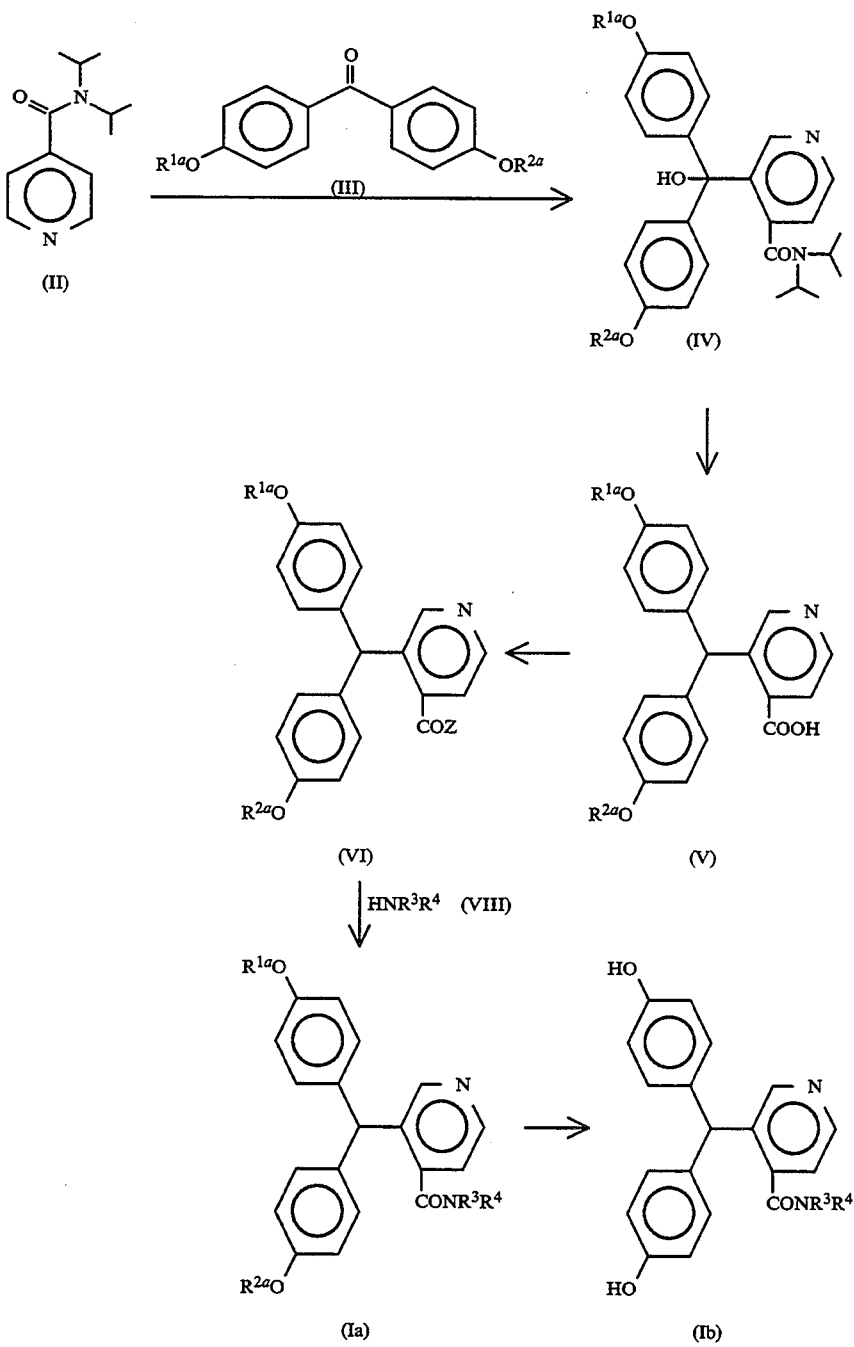

wherein R$^{1a}$ and R$^{2a}$ represent other groups denoted by R$^1$ and R$^2$ than hydrogen, respectively; Z represents chlorine or bromine; and R$^1$, R$^2$, R$^3$ and R$^4$ have the same meanings as previously defined.

Compound (II) is obtained by reacting isonicotinic acid with a halogenating agent such as thionyl chloride, phosphorus pentachloride, phosphorus trichloride or phosphorus tribromide to prepare an acid halide and condensing the acid halide with diisopropyl amine. Compound (IV) is obtained by reacting Compound (II) with 0.5 to 5 equivalents of an alkyl metal such as n-butyllithium or lithium diisopropylamide for from 30 minutes to 5 hours in an inert solvent, for example, an ether such as diethyl ether, tetrahydrofuran or the like at a temperature of −78° C. to 0° C., and then reacting the reaction product with Compound (III) at a temperature of −78° C. to room temperature for 30 minutes to 5 hours. The reaction is preferably carried out in a dry atmosphere of an inert gas such as nitrogen gas, argon gas or helium gas.

Compound (V) is obtained from Compound (IV) by catalytic reduction with palladium-carbon or the like as catalyst.

The reaction is usually completed in 10 minutes to 48 hours in, for example, an organic acid such as acetic acid, formic acid or the like at a temperature of room temperature to the boiling point of the solvent.

If desired, the reaction may be carried out in an organic acid mixed with a solvent, for example, an aromatic hydrocarbon such as benzene, toluene, xylene, etc.; an alcohol such as methanol, ethanol, isopropanol, etc.; an ether such as diethyl ether, dioxane, tetrahydrofuran; an amide such as formamide, dimethylformamide; acetonitrile, dimethylsulfoxide, water or the like.

Compound (VI) is obtained by reacting Compound (V) with a halogenating agent to give an acid halide. As the hylogenating agent, mention may be made of thionyl chloride, phosphorus pentachloride, phosphorus trichloride, phosphorus tribromide, etc. The halogenating agent may be used in an amount of 1 to 20 equivalents based on Compound (V) or in a large excessive amount in the case where it serves also as a reaction solvent. Any reaction solvent is used, so long as it does not participate in the reaction, and a halogenated hydrocarbon such as dichloromethane, chloroform, dichloroethane, carbon tetrachloride or the like may be used. The reaction is usually completed in 10 minutes to 24 hours at a temperature of 0° C. to the boiling point of the solvent.

Compound (Ia) which is Compound (I) where $R^1$ and $R^2$ are lower alkyl, is obtained by reacting Compound (VI) with Compound (VII). Compound (VII) is used in an amount of 0.1 to 5 equivalents, preferably 0.5 to 2 equivalents based on Compound (VI). Any reaction solvent is used alone or in admixture so long as it does not participate in the reaction. The reaction solvent, for example, includes a halogenated hydrocarbon such as dichloromethane, chloroform, dichloroethane and carbon tetrachloride; an aromatic hydrocarbon such as benzene, toluene and xylene; a ketone such as acetone and methyl ethyl ketone; an alcohol such as methanol, ethanol and isopropanol; an ether such as diethyl ether, dioxane and tetrahydrofuran; an amide such as formamide and dimethylformamide; acetonitrile, ethyl acetate, dimethylsulfoxide, pyridine, water or the like. In addition, in order to accelerate the reaction it is sometimes preferred to carry out the reaction in the presence of an inorganic base such as sodium hydroxide, potassium hydroxide, sodium carbonate, cesium carbonate, sodium bicarbonate or silver oxide; or an organic base such as triethylamine, N,N-diisopropyl ethylamine, N-methylmorpholine, pyridine and dimethylaminopyridine. The reaction is usually completed in 10 minutes to 48 hours at a temperature of 0° C. to the boiling point of the solvent.

In the case where Compound (Ib) which is Compound (I) where $R^1$ and $R^2$ are hydrogen, is desired to obtain, Compound (Ia) is dealkylated in the presence of, for example, a Lewis acid such as boron tribromide. The reaction solvent available for use includes a halogenated hydrocarbon such as dichloromethane, chloroform, dichloroethane, carbon tetrachloride or the like. The reaction is usually completed in 30 minutes to 5 hours at a temperature of −78° C. to room temperature.

The intermediates and object compounds prepared in accordance with the above processes can be isolated and purified by any purification methods conventionally used in the synthetic organic chemistry, for example, filtration, extraction, washing, drying, concentration, recrystallization, various chromatographies, etc. It is possible to use the intermediates as such in the subsequent reaction step without subjecting them to any purification procedures.

If a salt of Compound (I) is desired to obtain the salt of Compound (I) may be purified as such in the case where it is obtained in the salt form, whereas, in the case where it is obtained in a free form, it may be dissolved or suspended in an appropriate solvent, followed by addition of an appropriate acid for the formation of a salt and subjecting the salt to isolation steps.

Compound (I) and a pharmaceutically acceptable salt thereof may also be present in form of adducts with water or various solvents. The adducts are also included in scope of the present invention.

Representative examples of Compound (I) are shown in Table 1.

TABLE 1

[Structure: diphenylmethyl-pyridine with $R^1O$ and $R^2O$ substituents on phenyl rings and $CONR^3R^4$ group]

| Compound No. | $R^1$ | $R^2$ | $-NR^3R^4$ |
|---|---|---|---|
| 1 | CH₃ | CH₃ | −NH−(noradamantyl) |
| 2 | CH₃ | CH₃ | −N(piperidinyl) |
| 3 | CH₃ | CH₃ | −NH−(adamantyl) |
| 4 | CH₃ | CH₃ | −NH−(adamantyl isomer) |
| 5 | CH₃ | CH₃ | −NH−(cyclooctyl) |
| 6 | CH₃ | CH₃ | −N(piperazinyl)−N−(2-chlorophenyl) |
| 7 | CH₃ | CH₃ | −N(piperazinyl)−N−(2-methoxyphenyl) |
| 8 | CH₃ | CH₃ | −N(morpholinyl) |

TABLE 1-continued

[Structure: bis(4-R¹O/R²O-phenyl)(pyridin-3-yl with CONR³R⁴)methane]

| Compound No. | R¹ | R² | —NR³R⁴ |
|---|---|---|---|
| 9 | H | H | —NH-(noradamantyl) |
| 10 | H | H | —N(piperidinyl) |
| 11 | H | H | —NH-(adamantyl) |
| 12 | H | H | —NH-(cyclooctyl) |
| 13 | H | H | —N(piperazinyl)-N-(2-chlorophenyl) |
| 14 | H | H | —NH-(adamantyl) |
| 15 | H | H | —NH-C₆H₄-OH |
| 16 | H | H | —N(piperazinyl)-N-(3-CF₃-phenyl) |
| 17 | H | H | —N(piperazinyl)-N-(4-Cl-phenyl) |
| 18 | H | H | —N(piperazinyl)-N-(3-chlorophenyl) |
| 19 | H | H | —N(piperazinyl)-N-(2-hydroxyphenyl) |
| 20 | H | H | —N(piperazinyl)-N-phenyl |
| 21 | H | H | —N(piperazinyl)-N-(3-methylphenyl) |
| 22 | H | H | —N(piperazinyl)-N-(pyrimidin-2-yl) |
| 23 | H | H | —N(piperazinyl)-N-(4-fluorophenyl) |
| 24 | H | H | —N(piperazinyl)-N-(pyridin-2-yl) |
| 25 | CH₃ | CH₃ | —N(thiomorpholinyl) |
| 26 | H | H | —N(thiomorpholinyl) |

The bone resorption-inhibiting effect of the compounds of the present invention is illustrated by the following experiment.

EXPERIMENT 1

Calvaria were aseptically removed from 5- to 6-day-old dd mice, washed with Dulbecco's modified phosphate-buffered saline not containing calcium and magnesium (product of Gibco Oriental Co.), and cut along the sagittal suture into left and right halves. Each half calvarium was cultured in 1.5 ml medium consisting of Dulbecco's modified Eagle medium (high glucose) (product of Gibco Oriental Co.) supplemented with 15% heat-inactivated (at 56° C. for 20 minutes) horse serum, 2.5% heat-inactivated fetal bovine serum, plus 1% antibiotic-antimycotic liquid. The test compound was dissolved in dimethylsulfoxide, and a 10 μl portion of the solution was added to the culture to the final concentrations of $3 \times 10^{-6}$M, $1 \times 10^{-5}$M and $3 \times 10^{-5}$M. PTH (parathyroid hormone) was dissolved in 0.15M sodium chloride (pH 3), and a 3 μl-portion of the resulting solution was added to the culture to the final concentration of $1 \times 10^{-8}$M. Cultures were incubated at 37° C. in a water-saturated atmosphere consisting of 5% $CO_2$ and 95% air. Typically, cultures were maintained for 96 hours and the media were changed at 48 hours. The test compound and PTH which had been processed in the same manner as described above were added thereto. In order to investigate the action of the test compound on PTH-induced calcium release (i.e. bone resorption) from bones, there were prepared 3 groups: control group, PTH treated group ($1 \times 10^{-8}$M) and test compound- and PTH-treated group ($3 \times 10^{-6}$M, $1 \times 10^{-5}$M, $3 \times 10^{-5}$M). Bone resorption was assessed by measuring the accumulation of calcium in the culture media collected at 96 hours of culturing. The total calcium concentrations were determined using Calcium C-Test Wako (product of Wako). The inhibition rate was calculated therefrom according to the equation given below and 50% inhibitory concentration ($IC_{50}$) was determined. The results are shown in Table 2.

$$\text{Inhibitory rate (\%)} = \frac{C_P - C_D}{C_P - C_O} \times 100$$

$C_O$: Total calcium concentration in the culture free from both PTH and test compound
$C_P$: Total calcium concentration in the culture treated with PTH only
$C_D$: Total calcium concentration in the culture treated with both PTH and test compound.

TABLE 2

| Compound No. | Bone resorption-inhibiting effect ($IC_{50}$: μM) |
| --- | --- |
| 9 | 18.6 |
| 10 | 19.2 |
| 11 | 20.3 |
| 12 | 11.6 |
| 13 | 6.0 |
| 15 | 75.6 |
| 16 | 7.1 |
| 17 | 24.9 |
| 18 | 14.0 |
| 19 | 8.9 |
| 20 | 75.6 |
| 21 | 8.5 |
| 22 | 19.6 |

EXPERIMENT 2

Acute Toxicity Test

A test compound was orally administered to three dd-strain male mice weighing 20±1 g. The minimum lethal dose (MLD) was determined by observing the mortality for 7 days after the administration.

The results are shown in Table 3.

TABLE 3

| Compound No. | MLD (mg/kg) |
| --- | --- |
| 6 | >300 |
| 13 | >1000 |
| 18 | >300 |

Compound (I) and pharmaceutically acceptable salts thereof are formulated into any form of conventionally employed preparations, for example, tablets, capsules, syrups, injections, drops, suppositories, etc., and administered either orally or parenterally including, for example, intramuscular injection, intravenous injection, dripping and intrarectal administration of suppositories. Such preparations for oral or parenteral administration are produced by any of the conventional method may contain, for example, various excipients, lubricants, binders, disintegrators, isotonicities, emulsifiers, etc.

As the carrier to be used in such preparations, mention may be made of water, distilled water for injection, physiological saline, glucose, fructose, saccharose, mannitol, lactose, starch, cellulose, methyl-cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, glycerine fatty acid esters, etc.

Effective dose and number of administration of Compound (I) or a pharmaceutically acceptable salt thereof may vary depending upon modes of administration, age and body weight, conditions, etc. of a patient but it is generally preferred to administer Compound (I) in a dose of 0.1 to 10 mg/kg by dividing into one to four times.

Embodiments of the present invention are illustrated by the following examples and reference examples.

EXAMPLE 1

N-(Tricyclo[3.3.1.0$^{3,7}$]non-3-yl)-3-[bis(4-methoxyphenyl)-methyl]-4-pyridinecarboxamide (Compound 1)

In 25 ml of methylene chloride and 25 ml of thionyl chloride was dissolved 10 g of Compound b obtained in Reference Example 2, and the solution was refluxed for 30 minutes. The reaction solution was concentrated to give 20 g of 3-bis(4-methoxyphenyl)methyl-4-pyridinecarbonyl chloride hydrochloride (Compound c) as a crude product.

To 10 ml of 1,2-dichloroethane solution containing 2 g of 3-aminotricyclo[3.3.1.0$^{3,7}$]nonane hydrochloride and 10 ml of triethylamine was added 4.64 g of Compound c at room temperature. Then the mixture was stirred for 7 hours, followed by addition of water thereto to separate the organic layer. The aqueous layer was extracted with chloroform, then combined with the organic layer, washed with a saturated sodium chloride and dried over anhydrous magnesium sulfate. After concentration under reduced pressure, 2.5 g of the desired compound was obtained as a solid.

Melting point: 110°-112° C. (ethanol/ether)

IR (KBr) cm$^{-1}$: 3540, 3255, 2932, 1651, 1512, 1258

NMR (DMSO-d$_6$) δ(ppm): 8.47 (1H,d), 8.29 (1H, s), 8.10 (1H, s), 7.21 (1H, d), 7.00 (4H, d), 6.79 (4H, d), 5.91 (1H, s), 3.78 (6H, s), 2.27–1.43 (13H, m)

In the following Examples 2 to 8 and 25, the desired compounds were obtained in a similar manner as in Example 1, except that the corresponding amines were used instead of 3-aminotricyclo[3.3.1.0$^{3,7}$]nonane hydrochloride.

EXAMPLE 2

1-{3-[Bis(4-methoxyphenyl)methyl]isonicotinyl}piperidine (Compound 2)

NMR (CDCl$_3$) δ(ppm): 8.47 (1H, d), 8.31 (1H, s), 7.05–6.74 (9H, m), 5.75 (1H, s), 3.77 (6H, s), 2.80–1.40 (10H, m)

EXAMPLE 3

N-(Tricyclo[3.3.1.1$^{3,7}$]dec-1-yl)-3-[bis(4-methoxyphenyl)-methyl]-4-pyridinecarboxamide (Compound 3)

Melting point: 109°–110° C. (isopropanol/ethyl acetate/hexane)

IR (KBr) cm$^{-1}$: 3550, 2900, 1660, 1510, 1258, 1249

NMR (CDCl$_3$) δ(ppm): 8.53 (1H, d), 8.22 (1H, s), 7.25 (1H, d), 6.98 (4H, d), 6.73 (4H, d), 5.93 (1H, s), 3.78 (6H, s), 2.05–1.64 (15H, m)

EXAMPLE 4

N-(Tricyclo[3.3.1.1$^{3,7}$]dec-2-yl)-3-[bis(4-methoxyphenyl)-methyl]-4-pyridinecarboxamide (Compound 4)

Melting point: 142°–143° C. (methanol/chloroform)
IR (KBr) cm$^{-1}$: 2900, 1660, 1514, 1246
NMR (CDCl$_3$) δ(ppm): 8.52 (1H, d), 8.26 (1H, s), 7.25 (1H, d), 6.98 (4H, d), 6.80(4H, d), 5.96 (1H, s), 4.10 (1H, m), 3.77 (6H, s), 1.79–1.32 (14H, m)

EXAMPLE 5

N-Cyclooctyl-3-[bis(4-methoxyphenyl)methyl]-4-pyridinecarboxamide (Compound 5)

Melting point: 70°–73° C. (methanol/ether)
IR (KBr) cm$^{-1}$: 2915, 1655, 1510, 1250
NMR (CDCl$_3$) δ(ppm): 8.48 (1H, d), 8.22 (1H, s), 7.23 (1H, d), 6.99 (4H, d), 6.81 (4H, d), 5.93 (1H, s), 5.40 (1H, d), 3.77 (6H, s), 1.83 (1H, s), 1.60–1.34 (14H, m)

EXAMPLE 6

1-(2-Chlorophenyl)-4-{[3-bis(4-methoxyphenyl)methyl]-isonicotinyl}piperazine (Compound 6)

Melting point: 94°–96° C. (methanol/chloroform/ether)
IR (KBr) cm$^{-1}$: 3350, 1661, 1538, 1467
NMR (CDCl$_3$) δ(ppm): 8.51 (1H, d), 8.20 (1H, s), 7.45–6.85 (13H, m), 5.72 (1H, s), 3.72 (3H, s), 3.69 (3H, s), 3.95–2.50 (8H, m)

EXAMPLE 7

1-(2-Methoxyphenyl)-4-{[3-bis(4-methoxyphenyl)methyl]-isonicotinyl}piperazine (Compound 7)

Melting point: 72°–75° C. (ethanol/ether)
IR (KBr) cm$^{-1}$: 1633, 1507, 1242
NMR (CDCl$_3$) δ(ppm): 8.51 (1H, d), 8.33 (1H, s), 7.11–6.61 (13H, m), 5.86 (1H, s), 3.82 (3H, s), 3.77 (3H, s), 3.72 (3H, s), 4.10–1.70 (8H, m)

EXAMPLE 8

1-{3-[Bis(4-methoxyphenyl)methyl]isonicotinyl}morpholine (Compound 8)

Melting point: 107°–110° C. (ethanol/ether)
IR (KBr) cm$^{-1}$: 2830, 1625, 1511, 1241
NMR (CDCl$_3$) δ(ppm): 8.52 (1H, d), 8.32 (1H, s), 7.07–6.77 (9H, m), 5.80 (1H, s), 3.78 (6H, s), 4.00–2.30 (8H, m)

EXAMPLE 9

N-(Tricyclo[3.3.1.0$^{3,7}$]non-3-yl)-3-[bis(4-hydroxyphenyl)methyl]-4-pyridinecarboxamide (Compound 9)

In 40 ml of methylene chloride was dissolved 2.5 g of Compound 1 obtained in Example 1, and the solution was cooled to from −5° to −15° C. Then, 20 ml of a hexane solution containing 1M boron tribromide was added thereto. The mixture was stirred at room temperature for two hours and thirty minutes. The reaction mixture was poured into a saturated aqueous sodium bicarbonate solution, followed by extraction with ethyl acetate. The extract was dried over anhydrous magnesium sulfate. The solvent was evaporated under reduced pressure, and the residue was purified by silica gel column chromatography to give 0.63 g of the desired compound as a solid.

Melting point: 218°–220° C. (methanol/chloroform/ether)

IR (KBr) cm$^{-1}$: 3300, 1660, 1515, 1260

NMR (DMSO-d$_6$)δ(ppm): 9.21 (2H, s), 8.43 (1H, d), 8.24 (1H, s), 8.11 (1H, s), 7.21 (1H, d), 6.85 (4H, d), 6.66 (4H, d), 5.80 (1H, s), 2.35–1.40 (13H, m)

In the following Examples 10 to 24 and 26, the desired compounds were obtained in a similar manner as in Example 9, except that the corresponding alkoxy compound was used.

EXAMPLE 10

1-{3-[Bis-4-hydroxyphenyl)methyl]isonicotinyl}piperidine (Compound 10)

Melting point: 83°–85° C. (ethanol/ether)
IR (KBr) cm$^{-1}$: 3180, 2864, 1640, 1541
NMR (DMSO-d$_6$) δ(ppm): 9.29 (2H, s), 8.45 (1H, d), 8.19 (1H, s), 7.21 (1H, d), 6.85 (4H, d), 6.68 (4H, d), 5.48 (1H, s), 2.90–1.10 (10H, m)

EXAMPLE 11

N-(Tricyclo[3.3.1.1$^{3,7}$]dec-1-yl)-3-[bis(4-hydroxyphenyl)methyl]-4-pyridinecarboxamide (Compound 11)

Melting point: 109°–110° C. (methanol/chloroform)
IR (KBr) cm$^{-1}$: 3250, 2850,1675, 1640, 1540
NMR (DMSO-d$_6$) δ(ppm): 9.21 (2H, s), 8.43 (1H, d), 8.16 (1H, s), 7.72 (1H, s), 7.18 (1H, d), 6.86 (4H, d), 6.69 (4H, d), 5.75 (1H, s), 1.99–1.55 (15H, m)

EXAMPLE 12

N-Cyclooctyl-3-[bis(4-hydroxyphenyl)methyl]-4-pyridinecarboxamide (Compound 12)

NMR (DMSO-d$_6$) δ(ppm): 9.21 (2H, s), 8.43 (1H, d), 8.22 (1H, d), 8.14 (1H, s), 7.18 (1H, d), 6.85 (4H, d), 6.66 (4H, d), 5.80 (1H, s), 3.80 (1H, m), 1.65–1.35 (14H, m)

EXAMPLE 13

1-(2-Chlorophenyl)-4-{[3--bis(4,hydroxyphenyl)methyl]isonicotinyl}piperazine (Compound 13)

Melting point: 118°–120° C. (methanol/ether)
IR (KBr) cm$^{-1}$: 1645, 1539, 1260
NMR (DMSO-d$_6$) δ(ppm): 9.31 (2H, d), 8.41 (1H, d), 8.19 (1H, s), 7.35–6.60 (13H, m), 5.60 (1H, s), 3.90–2.50 (8H, m)

EXAMPLE 14

N-(Tricyclo[3.3.1.1$^{3,7}$]dec-2-yl)-3-[bis(4-hydroxyphenyl)methyl]4-pyridinecarboxamide (Compound 14)

NMR (CDCl$_3$) δ(ppm): 9.24 (2H, s), 8.41 (1H, d), 8.27 (1H, s), 8.10 (1H, S), 7.21 (1H, d), 6.85 (4H, d), 6.67 (4H, d), 5.81 (1H, s), 2.50–1.45 (14H, m)

EXAMPLE 15

N-(4-Hydroxyphenyl)-3-[bis(4-hydroxyphenyl)methyl]-4-pyridinecarboxamide (Compound 15)

IR (KBr) cm$^{-1}$: 3360, 1610, 1515, 1445, 1165
NMR (DMSO-d$_6$) δ(ppm): 10.30 (1H, s), 9.41–9.05 (3H, br), 8.55–8.40 (1H, m), 8.35–8.10 (1H, m), 7.55–7.15 (3H, m), 7.00–6.50 (10H, m), 5.80 (1H, s)

EXAMPLE 16

1-(3-Trifluoromethylphenyl)-4-{[3-bis(4-hydroxyphenyl)methyl]isonicotinyl}piperazine (Compound 16)

Melting point: 168°–170° C. (ethyl acetate)
IR (KBr) cm$^{-1}$: 3350, 1640, 1510, 1455
NMR (DMSO-d$_6$)δ(ppm): 9.45–9.10 (2H, br), 8.45 (1H, d), 8.18 (1H, s), 7.55–7.25 (1H, m), 7.29 (1H, d), 7.20–6.95 (3H, m), 6.87 (4H, d), 6.77 (4H, d), 5.55 (1H, s), 3.80–3.40 (2H, m), 3.35–2.70 (3H, m), 2.70–2.20 (3H, m)

EXAMPLE 17

1-(4-Chlorophenyl)-4-{[3-bis(4-hydroxyphenyl)methyl]isonicotinyl}piperazine (Compound 17)

Melting point: 243°–245° C. (methanol/ether)
IR (KBr) cm$^{-1}$: 3350, 1620, 1510, 1495, 1440, 1235
NMR (DMSO-d$_6$) δ(ppm); 9.90–8.90 (2H, br), 8.47 (1H, d), 8.17 (1H, s), 7.25 (1H, d), 7.20 (2H, d), 7.00–6.35 (10H, m), 5.55 (1H, s), 3.75–2.60 (8H, m)

EXAMPLE 18

1-(3-Chlorophenyl)-4-{[3-bis(4-hydroxyphenyl)methyl]isonicotinyl}piperazine (Compound 18)

Melting point: 252°–253° C. (ethyl acetate)
IR (KBr) cm$^{-1}$: 3350, 1620,1505, 1250
NMR (DMSO-d$_6$) δ(ppm): 9.25 (2H, s), 8.47 (1H, d), 8.19 (1H, s), 7.40–6.95 (3H, m), 7.05–6.55 (10H, m), 5.54 (1H, s), 3.75–3.40 (2H, m), 3.40–2.70 (3H, m), 2.70–2.10 (3H, m)

EXAMPLE 19

1-(2-Hydroxyphenyl)-4-{[3-bis(4-hydroxyphenyl)methyl]isonicotinyl}piperazine (Compound 19)

Melting point: 167°–169° C. (methanol/chloroform)
IR (KBr) cm$^{-1}$: 3260, 1615,1510, 1455, 1445, 1235
NMR (DMSO-d$_6$) δ(ppm): 9.30 (1H, s), 9.25 (1H, s), 8.85 (1H, s), 8.45 (1H, d), 8.15 (1H, s), 7.25 (1H, d), 7.00–6.55 (12H, m), 5.57 (1H, s), 3.80–3.40 (2H, m), 3.20–2.80 (2H, m), 2.80–2.40 (4H, m)

EXAMPLE 20

1-Phenyl-4-{[3-bis(4-hydroxyphenyl)methyl]isonicotinyl}piperazine (Compound 20)

Melting point: 253°–255° C. (methanol/chloroform)
IR (KBr) cm$^{-1}$: 3400, 1620, 1595, 1505, 1230
NMR (DMSO-d$_6$) δ(ppm): 9.27 (2H, s), 8.45 (1H, d), 8.17 (1H, s), 7.35–6.95 (3H, m), 6.95–6.55 (11H, m), (1H, 5.53 (1H, s), 3.75–3.45 (2H, m), 3.25–2.65 (3H, m), 2.65–2.15 (3H, m)

EXAMPLE 21

1-(3-Methylphenyl)-4-{[3-bis(4-hydroxyphenyl)methyl]isonicotinyl}piperazine (Compound 21)

Melting point: 229°–230° C. (methanol/ether)
IR (KBr) cm$^{-1}$: 3350, 1625, 1610, 1510, 1245
NMR (DMSO-d$_6$) δ(ppm): 9.20 (2H, s), 8.43 (1H, d), 8.15 (1H, s), 7.25 (1H, d), 7.20–6.85 (2H, m), 6.95–6.70 (1H, m), 6.73 (4H, d), 6.63 (4H, d), 6.65–6.45 (1H, m), 5.49 (1H, s), 3.70–3.45 (2H, m), 3.15–2.40 (6H, m), 2.20 (3H, s)

EXAMPLE 22

1-(2-Pyrimidyl)-4-{[3-bis(4-hydroxyphenyl)methyl]isonicotinyl}piperazine (Compound 22)

Melting point: 173°–175° C. (methanol/ether)
IR (KBr) cm$^{-1}$: 3375, 1620, 1580, 1510, 1437, 1255
NMR (DMSO-d$_6$) δ(ppm): 8.65–8.35 (1H, m), 8.35 (1H, s), 8.30 (1H, s), 8.30–8.10 (1H, br), 7.35 (1H, d), 7.00–6.50 (3H, m), 6.77(4H, d), 6.67 (4H, d), 5.55 (1H, s), 3.70–3.10 (6H, m), 3.10–2.40 (2H, m)

EXAMPLE 23

1-(4-Fluorophenyl)-4-{[3-bis(4-hydroxyphenyl)methyl]isonicotinyl}piperazine (Compound 23)

Melting point: 165°–167° C. (methanol/ether)
IR (KBr) cm$^{-1}$: 1610, 1510, 1445, 1230, 1020, 830
NMR (DMSO-d$_6$) δ(ppm): 9.25 (2H, s), 8.45 (1H, d), 8.18 (1H, s), 7.28 (1H, d), 7.15–6.60 (12H, m), 5.55 (1H, s), 3.70–3.50 (2H, m), 3.15–2.40 (6H, m)

EXAMPLE 24

1-(2-Pyridyl)-4-{[3-bis(4-hydroxyphenyl)methyl]isonicotinyl}piperazine (Compound 24)

Melting point; 283°–284° C. (methanol/ether)
IR (KBr) cm$^{-1}$: 3000, 1630, 1595, 1510, 1435, 1240, 825
NMR (DMSO-d$_6$) δ(ppm): 9.28 (2H, s), 8.46 (1H, d), 8.19 (1H, s), 8.08 (1H, dd), 7.50 (1H, ddd), 7.27 (1H, d), 6.95–6.50 (10H, m), 5.53 (1H, s), 3.65–2.85 (8H, m)

EXAMPLE 25

1-{3-[Bis(4-methoxyphenyl)methyl]isonicotinyl}thiomorpholine (Compound 25)

Melting point: 117°–120° C.
IR (KBr) cm$^{-1}$: 2915, 1625, 1510, 1255
NMR (CDCl$_3$) δ(ppm): 8.50 (1H, d), 8.32 (1H, s), 7.10–6.93 (5H, m), 6.89–6.78 (4H, m), 5.73 (1H, s), 4.12–4.04 (1H, m), 3.80 (3H, s), 3.78 (3H, s), 3.71–3.58 (1H, m), 3.15–3.03 (1H, m); 2.71–2.47 (3H, m),2.28–2.19 (1H, m), 1.71–1.65 (1H, m)

EXAMPLE 26

1-{3-[Bis(4-hydroxyphenyl)methyl]isonicotinyl}thiomorpholine (Compound 26)

Melting point: 225°–226° C.

IR (KBr) cm$^{-1}$: 3260, 1613, 1518, 1443

NMR (DMSO-d$_6$) δ(ppm): 9.38 (1H, s), 9.32 (1H, s), 8.46 (1H, d), 8.18 (1H,s), 7.29 (1H,d), 6.89–6.74 (4H, m), 6.74–6.64 (4H, m), 5.45 (1H, s), 4.05–3.90 (1, m), 3.50–3.35 (1H, m), 3.10–2.95 (1H, m), 2.70–2.33 (4H, m), 1.85–1.70 (1H, m)

REFERENCE EXAMPLE 1

3-[1-Hydroxy-1,1-bis(4-methoxyphenyl)methyl]-N,N-diisopropyl-4-pyridinecarboxamide (Compound a)

In 480 ml of dry tetrahydrofuran was dissolved 81.5 ml of diisopropylamine under nitrogen atmosphere, and the solution was cooled to −70° C. Then, 375 ml of 1.6N n-butyllithium was dropwise added to the extent that the temperature of the mixture was not higher than −65° C., to thereby produce lithium diisopropylamide. The reaction mixture was kept at −70° C. for one hour, and to the reaction mixture was added a solution of 43.97 g of N,N-diisopropylisonicotinamide in 150 ml of dry tetrahydrofuran, to the extent that the temperature of the mixture was not higher than −65° C. The mixture was stirred for one hour and 15 minutes, and to the reaction mixture was dropwise added a solution of 46.94 g of 4,4'-dimethoxybenzophenone in 945 ml of dry tetrahydrofuran to the extent that the temperature of the mixture was not higher than −65° C., followed by stirring for 15 minutes. Thereafter, the temperature was allowed to be brought back to room temperature, and water was added thereto. After extraction with ethyl acetate, the extract was dried over anhydrous magnesium sulfate. The solvent was distilled off under reduced pressure, and the resulting residue was purified by silica gel column chromatography to give 63.69 g of the desired compound as a solid.

NMR (CDCl$_3$) δ(ppm): 8.53 (1H, d), 8.14 (1H, s), 7.28–7.05 (5H, m), 6.80 (4H, d), 6.14 (1H, d), 3.79 (6H, s), 3.59 (1H, m), 3.35 (1H, m), 1.43 (3H, d), 1.17 (3H, d), 1.16 (3H, d), 0.85 (3H, d)

REFERENCE EXAMPLE 2

3-Bis(4-methoxyphenyl)methyl-4-pyridinecarboxylic Acid (Compound b)

In 1,000 ml of acetic acid was dissolved 103.38 g of Compound a obtained in Reference Example 1, and to the solution was added 15 g of 10% palladium-carbon suspended in 200 ml of water. The mixture was stirred under hydrogen atmosphere at 70° C. for 8 hours and 15 minutes. The reaction mixture was filtered with a filter aid, and the filtrate was concentrated and crystallized with water to give 45.19 g of the desired compound.

Melting point: 122°–124° C. (acetic acid/water)

IR (KBr) cm$^{-1}$: 1609, 1511, 1250

NMR (DMSO-d$_6$) δ(ppm): 8.57 (1H, d), 8.22 (1H, s), 7.63 (1H, d), 7.04–6.81 (8H, m), 6.33 (1H, s), 3.73 (6H, s)

What is claimed is:

1. A pyridine derivative represented by the following formula:

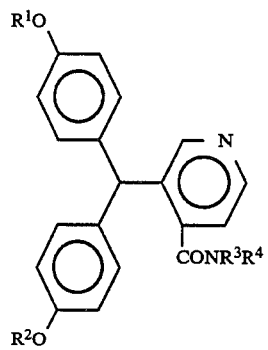

wherein each of R$^1$ and R$^2$ independently represents hydrogen or lower alkyl; and each of R$^3$ and R$^4$ independently represents hydrogen, lower alkyl, alicyclic alkyl having 3 to 8 carbon atoms, substituted or unsubstituted polycyclic alkyl having the structural formula:

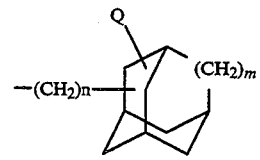

wherein Q represents hydrogen or lower alkyl; m is an integer of 0 or 1; and n is an integer of 0 to 5; or the structural formula:

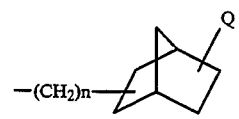

wherein Q and n have the same significance as defined above; substituted or unsubstituted aryl wherein substituents are independently selected from the group consisting of lower alkyl, hydroxy, lower alkoxy, lower alkylthio, halogen, nitro, amino, lower alkanoyl, aroyl, carboxyl, lower alkoxycarbonyl, trifluoromethyl; or R$^3$ and R$^4$ are combined with nitrogen atom adjacent thereto to form a substituted or unsubstituted 4-phenyl-, 4-pyrimidinyl-, or 4-pyridyl-substituted piperazinyl, piperidino, morpholino, or thiomorpholino wherein substituents are independently selected from the group consisting of lower alkyl, hydroxy, lower alkoxy, lower alkylthio, halogen, nitro, amino, lower alkanoyl, aroyl, carboxyl, lower alkoxycarbonyl, trifluoromethyl; or a pharmaceutically acceptable salt thereof.

2. The compound according to claim 1, wherein R$^1$ and R$^2$ are hydrogen or methyl.

3. The compound according to claim 1, wherein R$^1$ and R$^2$ are hydrogen and R$^3$ and R$^4$ are combined with nitrogen atom adjacent thereto to form a substituted or unsubstituted 4-phenyl-, 4-pyrimidinyl-, or 4-pyridyl-substituted piperazinyl.

4. The compound according to claim 3, wherein the substituents of the substituted phenyl are a member consisting of lower alkyl, hydroxy, alkoxy, halogen and trifluoromethyl.

5. The compound according to claim 4, wherein the halogen is chlorine.

6. 1-(2-Chlorophenyl)-4-{[3-bis(4-hydroxyphenyl)-methyl]-isonicotinyl}piperazine, or a pharmaceutically acceptable salt thereof.

7. A pharmaceutical composition for treating osteoporisis comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 5,374,634
DATED : December 20, 1994
INVENTOR(S) : IWAO KINOSHITA ET AL.

It is certified that error appears in the above-indentified patent and that said Letters Patent is hereby corrected as shown below:

COLUMN 2

Line 22, "alkanoyI," should read --alkanoyl,--.

COLUMN 15

Line 51, "Acid" should read --acid--.

COLUMN 16

Line 65, "teoporisis" should read --teoporosis--.

Signed and Sealed this

Second Day of May, 1995

Attest:

BRUCE LEHMAN

Attesting Officer     Commissioner of Patents and Trademarks